(12) United States Patent
Saudan et al.

(10) Patent No.: US 8,692,022 B2
(45) Date of Patent: *Apr. 8, 2014

(54) HYDROGENATION OF ESTERS WITH RU/BIDENTATE LIGANDS COMPLEXES

(75) Inventors: Lionel Saudan, Geneva (CH); Philippe Dupau, Bellegarde/Valserine (FR); Jean-Jacques Riedhauser, Dardagny (CH); Patrick Wyss, Romont (CH)

(73) Assignee: Firmenich SA, Geneva (CH)

( * ) Notice: Subject to any disclaimer, the term of this patent is extended or adjusted under 35 U.S.C. 154(b) by 489 days.

This patent is subject to a terminal disclaimer.

(21) Appl. No.: 12/839,787

(22) Filed: Jul. 20, 2010

(65) Prior Publication Data
US 2010/0280273 A1  Nov. 4, 2010

Related U.S. Application Data

(63) Continuation-in-part of application No. 11/854,106, filed on Sep. 12, 2007, now Pat. No. 7,763,758, which is a continuation of application No. PCT/IB2006/051027, filed on Apr. 4, 2006.

(30) Foreign Application Priority Data

Apr. 5, 2005 (WO) .................. PCT/IB2005/000938

(51) Int. Cl.
*C07F 9/28* (2006.01)
(52) U.S. Cl.
USPC .............................................. 568/10; 564/15

(58) Field of Classification Search
USPC .................................. 548/400; 568/10; 564/15
See application file for complete search history.

(56) References Cited

U.S. PATENT DOCUMENTS

| | | |
|---|---|---|
| 2004/0015017 A1 | 1/2004 | Rautenstrauch et al. ..... 564/490 |
| 2004/0063966 A1* | 4/2004 | Rautenstrauch et al. ..... 548/400 |

FOREIGN PATENT DOCUMENTS

| | | |
|---|---|---|
| GB | 2 031 883 A | 4/1980 |
| WO | WO 02/22526 A2 | 3/2002 |
| WO | WO 02/40155 A1 | 5/2002 |

OTHER PUBLICATIONS

Gao et al., "New Chiral Catalysts for Reduction of Ketones", Chirality, 12:383-388 (2000).
Kerkadze, "Effect of new complex chemical mutagens on citrus ovaries and the analysis of their seed progeny," Genetika (Moscow), 1968, 4(2):33-40 (abstract only).
International Search Report and Written Opinion of the International Searching Authority, Application No. PCT/IB2006/051028, dated Aug. 9, 2006.

* cited by examiner

*Primary Examiner* — Yong Chu
*Assistant Examiner* — Sonya Wright
(74) *Attorney, Agent, or Firm* — Winston & Strawn LLP

(57) ABSTRACT

The present invention relates to the field of catalytic hydrogenation and, more particularly, to the use of Ru complexes with bidentate ligands, having one amino or imino coordinating group and one phosphino coordinating group, in hydrogenation processes for the reduction of esters or lactones into the corresponding alcohol or diol respectively.

16 Claims, No Drawings

HYDROGENATION OF ESTERS WITH RU/BIDENTATE LIGANDS COMPLEXES

CROSS-REFERENCE TO RELATED APPLICATION(S)

This application is a continuation-in-part of application Ser. No. 11/854,106 filed Sep. 12, 2007 now U.S. Pat. No. 7,763,758, which is a continuation of International application PCT/IB2006/051027 filed on Apr. 4, 2006, the entire content of each of which is expressly incorporated herein by reference thereto.

TECHNICAL FIELD

The present invention relates to the field of catalytic hydrogenation and, more particularly, to the use of Ru complexes with bidentate ligands, in hydrogenation processes for the reduction of esters or lactones into the corresponding alcohol or diol respectively.

BACKGROUND

Reduction of an ester functional group to the corresponding alcohol is one of the fundamental reactions in organic chemistry, and is used in a large number of chemical processes. In general, two main types of processes are known to achieve such a transformation. Such types of processes are the following:
a) hydride processes, in which a silyl or metal hydride salt, such as $LiAlH_4$, is used;
b) hydrogenation processes, in which molecular hydrogen is used.

From a practical point of view, hydrogenation processes are more attractive as they can be run using small amounts of catalyst (typically 10 to 1000 ppm relative to the substrate) and in the presence of small quantities or even in the absence of solvent. Furthermore, hydrogenation processes do not require the use of highly reactive and expensive hydrides, and do not produce important amounts of aqueous waste.

One of the mandatory and characterizing elements of hydrogenation processes is the catalyst or the catalytic system which is used to activate the molecular hydrogen in view of the reduction. The development of useful catalysts or catalytic systems for the hydrogenation of an ester functional group represents still an important need in chemistry.

Amongst the few catalysts or catalytic systems known to perform such reductions one may cite the ruthenium/phosphine complexes, obtained by the reaction of ruthenium oxide or carboxylate precursor with a mono-, di- or tri-phosphine ligand (an example of which is described by Elsevier et al. in Chem. Commun., 1998, 1367). In this type of complex the ruthenium metal is coordinated only by "acac" ligands and phosphine atoms, limiting thus the diversity of the ligand structure and coordination sphere around the metal center. As a consequence of such little diversity the tuning of the activity and of the performance of the hydrogenation process is not easy. Furthermore, the experimental conditions require very high pressures (at least 70-130 bars) and temperatures (120-180° C.).

Therefore, there is a need for hydrogenation processes using alternative catalysts or pre-catalysts, preferably having a greater diversity in the ligand structures and coordination spheres around the metal center and allowing the use of softer experimental conditions.

SUMMARY OF THE INVENTION

The present invention now relates about a hydrogenation process for the reduction of esters, or the like, into alcohols in the presence of a base and at least one complex in the form of a ruthenium complex of a bidentate ligand wherein the coordinating groups consist of one amino or imino group and one phosphino group. The invention relates also about new ligands and complexes useful for carrying the invention process.

DETAILED DESCRIPTION OF THE PREFERRED EMBODIMENTS

In order to overcome the problems aforementioned, the present invention relates to processes for the reduction by hydrogenation, using molecular $H_2$, of a $C_3$-$C_{70}$ substrate containing one or two esters, or lactones, functional groups into the corresponding alcohol, or diol, characterized in that the process is carried out in the presence of a base and at least one catalyst or pre-catalyst in the form of a ruthenium complex of a bidentate ligand wherein the coordinating groups consist of one amino or imino group and one phosphino group.

According to an embodiment of the invention, the amino group is a primary (i.e. $NH_2$) or a secondary (i.e. NH) amino group.

According to a particular embodiment of the invention, the substrate can be a compound of formula (I)

wherein $R^a$ and $R^b$ represent, simultaneously or independently, a linear, branched or cyclic $C_1$-$C_{30}$ aromatic, alkyl or alkenyl group, optionally substituted; or $R^a$ and $R^b$ are bonded together and form a $C_4$-$C_{20}$ saturated or unsaturated group, optionally substituted.

The corresponding alcohols (i.e., (II-a) and (II-b)), or the corresponding diol (II'), of the substrate (I), are of formula

wherein $R^a$ and $R^b$ are defined as in formula (I).

A compound of formula (II) (i.e. II-a or II-b) will be obtained in the case where $R^a$ and $R^b$ are not bonded together, while a compound of formula (II') will be obtained in the case where $R^a$ and $R^b$ are bonded together.

It is understood that by "a linear, branched or cyclic ... aromatic, alkyl, or alkenyl group" it is meant that the $R^a$ or $R^b$ can be in the form of, e.g., a linear alkyl group or can also be in the form of a mixture of the type of groups, e.g. a specific $R^a$ may comprise a linear alkyl, a branched alkenyl, a (poly) cyclic alkyl and an aryl moiety, unless a specific limitation to only one type is mentioned. Similarly, in all the below embodiments of the invention when a group is mentioned as being in the form of more than one type of topology (e.g. linear, cyclic or branched) and/or unsaturation (e.g. alkyl, aromatic or alkenyl) it is meant also a group which may comprise moieties having any one of the topologies or unsaturations, as above explained.

A particular embodiment of the invention's process is shown in Scheme 1:

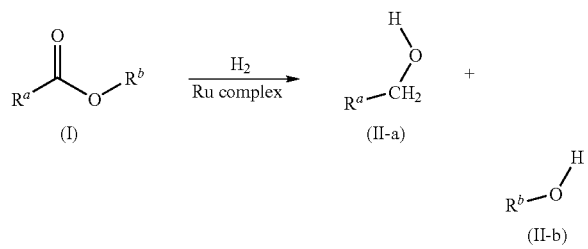

According to a further embodiment of the invention, the substrate is an ester, or lactone, that will provide an alcohol, or a diol, that is useful in the pharmaceutical, agrochemical or perfumery industry as final product or as an intermediate. Particularly preferred substrate is an ester, or lactone, that will provide an alcohol, or diol, which is useful in the perfumery industry as final product or as an intermediate.

According to another embodiment of the invention, the substrate is a $C_5$-$C_{30}$ compound of formula (I), and in particular one may cite those wherein $R^a$ and $R^b$ represent simultaneously or independently a linear, branched or cyclic $C_1$-$C_{30}$ aromatic or alkyl group optionally substituted, or a cyclic $C_5$-$C_{30}$ alkenyl group optionally substituted; or $R^a$ and $R^b$ are bonded together and form a $C_4$-$C_{20}$ saturated or unsaturated linear, branched, mono-, di- or tri-cyclic group, optionally substituted.

According to a further embodiment of the invention the substrate is a $C_5$-$C_{20}$ compound of formula (I), wherein $R^a$ and $R^b$ represent simultaneously or independently a linear, branched or cyclic $C_5$-$C_{18}$ aromatic or alkyl group, optionally substituted, or a cyclic $C_5$-$C_{18}$ alkenyl group, optionally substituted; or $R^a$ and $R^b$ are bonded together and form a $C_4$-$C_{20}$ saturated or unsaturated linear, branched, mono-, di- or tri-cyclic group, optionally substituted.

Furthermore, according to a yet further embodiment, when $R^a$ and/or $R^b$ represent an alkenyl group then the carbon-carbon double bond is not terminal and is not conjugated.

Possible substituents of $R^a$ and $R^b$ are one, two or three halogen, $OR^c$, $NR^c_2$ or $R^c$ groups, in which $R^c$ is a hydrogen atom, a halogenated $C_1$-$C_2$ group or a $C_1$ to $C_{10}$ cyclic, linear or branched alkyl, or alkenyl group, preferably a $C_1$ to $C_4$ linear or branched alkyl or alkenyl group. As other possible substituents one may also cite a group $COOR^c$, which can also be reduced to the corresponding alcohol during the invention's process, according to the molar amount of $H_2$ used, as well known by a person skilled in the art.

Non-limiting examples of substrates are alkyl cinnamates, sorbates or salycilates, alkyl esters of natural (fatty or not) acids, Sclareolide, spirolactones, allylic ester, di alkyl diesters, (un)substituted benzoic esters, and β-γ unsaturated esters. In particular, the substrate can be selected from the group consisting of sclareolide, $C_9$-$C_{15}$ spirolactones and $C_1$-$C_4$ alkyl esters of 4-methyl-6-(2,6,6-trimethyl-1-cyclohexen-1-yl)-3-hexenoic acid. One can also cite the di alkyl esters of 1,4-dicarboxylate-cyclohexane, the di $C_{1-5}$ alkyl esters of the $C_{2-10}$ alkanediyl-dicarboxylates, $C_{1-5}$ alkyl cyclopropanecarboxylates, mono-, di- or tri-methoxybenzoic esters.

The process of the invention is characterized by the use, as catalyst or pre-catalyst (hereinafter referred to as complexes unless specified otherwise), of a ruthenium complex as described above. The complex can be in the form of an ionic or neutral species.

According to an embodiment of the invention, the ruthenium complex can be of the general formula $$[Ru(L2)_b(L')_aY_2] \qquad (1)$$

wherein L2 represents a bidentate ligand wherein the coordinating groups consist of one amino or imino group and one phosphino group;

L' represents a $C_3$-$C_{70}$ mono-phosphine (L1-P) or a molecule of solvent (L1-S);

b is 1 and a is 1 or 2 or b is 2 and a is 0; and each Y represents, simultaneously or independently, CO, a hydrogen or halogen atom, a hydroxyl group, or a $C_1$-$C_6$ alkoxy or carboxylic radical. Alternatively, Y may also represent a $BH_4$ or $AlH_4$ group.

In a particular embodiment of the invention the L2 ligand may be a $C_4$-$C_{40}$ compound.

In a particular embodiment of the invention, in formula (1), each Y represents, simultaneously or independently, a hydrogen or chlorine atom, a hydroxy radical, a $C_1$ to $C_6$ alkoxy radical, such as a methoxy, ethoxy or isopropoxy radical, or a $C_1$ to $C_6$ acyloxy radical such as a $CH_3COO$ or $CH_3CH_2COO$ radical. More preferably, each Y represents, simultaneously or independently, a hydrogen or chlorine atom, a methoxy, ethoxy or isopropoxy radical, or a $CH_3COO$ or $CH_3CH_2COO$ radical.

Y may also be a solvent, the term "solvent" has to be understood according to the usual meaning in the art and includes compounds used as diluent in the preparation of the complex or during the invention's process, non limiting examples are dimethylsulfoxide, acetonitrile, dimethylformamide, an alcohol (e.g. an $C_1$-$C_4$ alcohol), or also THF, acetone, pyridine or a $C_3$-$C_8$ ester or the substrate of the invention's process.

According to a particular embodiment of the invention, there can be used as complex a compound of one of the formulae $$[Ru(L2)_2Y_2] \qquad (2)$$

$$[Ru(L2)(L1\text{-}P)_c(L1\text{-}S)_{2-c'}Y_2] \qquad (2')$$

wherein L2 and Y have the meaning indicated above, c is 1 or 2, and c' is 0, 1 or 2.

The complexes of formula (2) represent a preferred embodiment of the invention.

According to any one of the above-mentioned embodiment, the bidentate ligand L2 can be a compound of one of the formulae

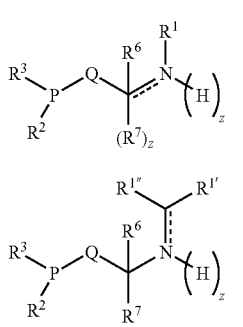

(2-A)

(2-A')

wherein the dotted line indicates a single or double bond;

z is 0 or 1 when the carbon-nitrogen bond with the dotted line represents a single or double bond respectively;

$R^1$ represents a hydrogen atom, a linear, branched or cyclic $C_1$ to $C_{10}$ alkyl or alkenyl group optionally substituted;

$R^{1'}$ and $R^{1''}$, when taken separately, represents a hydrogen atom, a linear, branched or cyclic $C_1$ to $C_9$ alkyl or alkenyl group optionally substituted or a $C_6$ to $C_{10}$ aromatic group optionally substituted; the $R^{1'}$ or $R^{1''}$, when taken together, form a saturated or unsaturated ring optionally substituted, having 5 to 12 atoms and including the carbon atom to which the $R^{1'}$ and $R^{1''}$ groups are bonded;

$R^2$ and $R^3$, when taken separately, represent, simultaneously or independently, a linear, branched or cyclic $C_1$ to $C_8$ alkyl or alkenyl group optionally substituted, a $C_6$ to $C_{10}$ aromatic group optionally substituted, or an $OR^{2'}$ or $NR^{2'}R^{3'}$ group, $R^{2'}$ and $R^{3'}$ being a $C_1$ to $C_8$ alkyl or alkenyl group; the groups $R^2$ and $R^3$, when taken together, may form a saturated or unsaturated ring optionally substituted, having 5 to 10 atoms and including the phosphorus atom to which the $R^2$ and $R^3$ groups are bonded;

$R^6$ and $R^7$ represent, simultaneously or independently, a hydrogen atom, a linear, branched or cyclic $C_1$ to $C_{10}$ alkyl or alkenyl group optionally substituted, a $C_6$-$C_{10}$ aromatic group optionally substituted, or an $OR^{4'}$ or $NR^{4'}R^{5'}$ group, $R^{4'}$ and $R^{5'}$ being a linear, branched or cyclic $C_1$ to $C_{10}$ alkyl or alkenyl group; $R^6$ and $R^1$ or $R^6$ and $R^{1''}$, taken together, may form a saturated or unsaturated heterocycle, optionally substituted and optionally containing one or two additional nitrogen or oxygen atoms, containing 5 to 10 atoms and including the carbon atoms and the N atom to which the $R^6$ or $R^1$, or $R^{1''}$, group are bonded respectively; and Q represents:

a group of formula (i)

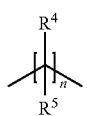

wherein n is an integer from 1 to 4, and $R^4$ and $R^5$ represent, simultaneously or independently, a hydrogen atom, a linear, branched or cyclic $C_1$ to $C_{10}$ alkyl or alkenyl group optionally substituted, a $C_6$-$C_{10}$ aromatic group optionally substituted, or an $OR^{4'}$ or $NR^{4'}R^{5'}$ group, $R^{4'}$ and $R^{5'}$ being a linear, branched or cyclic $C_1$ to $C_{10}$ alkyl or alkenyl group;

two distinct $R^4$ and/or $R^5$ groups, taken together, may form a $C_5$ to $C_8$, or even up to $C_{10}$, saturated ring optionally substituted, including the carbon atoms to which each of the $R^4$ or $R^5$ group is bonded; or a group of formula (ii)

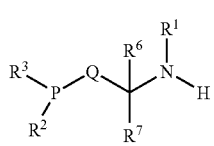

wherein n is an integer from 2 to 4, and two distinct adjacent $R^4$ groups, taken together, form a $C_5$ to $C_8$, or even up to $C_{10}$, aromatic ring optionally substituted or a $C_5$-$C_{12}$ metallocenediyl optionally substituted, including the carbon atoms to which each of the $R^4$ group are bonded; or three distinct adjacent $R^4$ groups, taken together, form a naphthalene ring optionally substituted, including the carbon atoms to which each of the $R^4$ groups are bonded.

According to en embodiment by "aromatic group or ring" it is meant a phenyl or naphthyl derivative.

According to another embodiment of the invention, Q represents a linear $C_2$-$C_5$ alkylene radical optionally substituted, a ferrocenediyl optionally substituted or a biphenyldiyl or binaphthildiyl radical optionally substituted.

Possible substituents of $R^{1'}$, $R^{1''}$ and $R^1$ to $R^7$ and Q are one or two halogen, $C_1$ to $C_{10}$ alkoxy or polyalkyleneglycols groups, halo- or perhalo-hydrocarbon, COOR, $NR_2$, quaternary amine or R groups, wherein R is a $C_1$ to $C_6$ alkyl, or a $C_5$ to $C_{12}$ cycloalkyl, aralkyl (such as benzyl, phenethyl etc.) or aromatic group, the latter being also optionally substituted by one, two or three halogen, sulfonates groups or $C_1$-$C_8$ alkyl, alkoxy, amino, nitro, sulfonates, halo- or perhalo-hydrocarbon or ester groups. By "halo- or perhalo-hydrocarbon" it is meant groups such as $CF_3$ or $CClH_2$ for instance.

To our surprise, the ligands of formula (2-A') are new, when the dotted line represents a double bong and z is 0, at the exception of 2-(diphenylphosphino)-N-(phenylmethylene)-cyclohexanamine, and therefore are also an object of the present invention.

The complexes according to the invention having as ligand a compound of formula (2-A'), when the dotted line represents a double bong and z is 0, are also new, at the exception of dichloro[[N(Z), 1R,2R]-2-(diphenylphosphino-κP)-N-(phenylmethylene)cyclohexanamine-κN](triphenylphosphine)-Ruthenium, and are therefore also another object of the present invention.

In a particular embodiment of formula (2-A), L2 is a bidentate N—P ligand of general formula (2-B)

in which $R^1$ represents a hydrogen atom, a linear, branched or cyclic $C_1$ to $C_6$ alkyl or alkenyl group optionally substituted; $R^2$ and $R^3$ represent, simultaneously or independently, a linear, branched or cyclic $C_1$ to $C_6$ alkyl group optionally substituted, a phenyl or naphthyl group optionally substituted; or the groups $R^2$ and $R^3$, taken together, form a saturated or unsaturated ring optionally substituted, having 5, 6 or 7 atoms and including the phosphorus atom to which the $R^2$ and $R^3$ groups are bonded;

$R^6$ and $R^7$ represent, simultaneously or independently, a hydrogen atom, a linear or branched $C_1$ to $C_4$ alkyl group optionally substituted, a phenyl ring optionally substituted; $R^6$ and $R^1$, taken together, may form a saturated or unsaturated heterocycle, optionally substituted and optionally containing one additional nitrogen or oxygen atoms, containing 5 or 6 atoms and including the carbon atoms and the N atom to which the $R^6$ or $R^1$ group are bonded respectively; and Q represents:

a group of formula

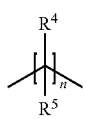

(iii)

wherein n is an integer from 2 or 3, and $R^4$ and $R^5$ represent, simultaneously or independently, a hydrogen atom, a linear or branched $C_1$ to $C_4$ alkyl group optionally substituted, a phenyl ring optionally substituted; or two distinct $R^4$ and/or $R^5$ groups, taken together, form a $C_5$ to $C_{10}$ saturated ring optionally substituted including the carbon atoms to which each of the $R^4$ or $R^5$ group is bonded; or a group of formula

(iv)

wherein n is an integer from 1 to 3, and two distinct adjacent $R^4$ groups, taken together, form a $C_5$ to $C_{10}$ aromatic ring optionally substituted or a $C_5$-$C_{12}$ ferrocenediyl optionally substituted, including the carbon atoms to which each of the $R^4$ group are bonded; or three distinct adjacent $R^4$ groups, taken together, form a naphthalene ring optionally substituted, including the carbon atoms to which each of the $R^4$ group are bonded.

Possible substituents of $R^1$ to $R^7$, in particular when the groups are or contain phenyl groups or moieties, are one or two halogen, $CF_3$ groups or $C_1$ to $C_5$ alkoxy or polyalkyleneglycols groups, COOR, $NR_2$ or R groups, wherein R is a $C_1$ to $C_4$ alkyl, or a $C_{5-6}$ cycloalkyl, aralkyl or aromatic group, the latter being also optionally substituted as above defined.

A particular embodiment of formula (2-B) is represented by formula (2-C) or (2-D)

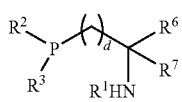

(2-C)

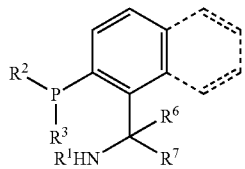

(2-D)

wherein the dotted lines in formula (2-D) indicate the presence of a phenyl or a naphthyl group;

d represents 1 or 2;

$R^1$ represents a hydrogen atom or a $C_1$ to $C_4$ linear or branched alkyl group possibly substituted;

$R^2$ and $R^3$ represent a linear, branched or cyclic $C_1$ to $C_6$ alkyl group optionally substituted or an phenyl group optionally substituted; and $R^6$ and $R^7$ represent, simultaneously or independently, a hydrogen atom, a linear or branched $C_1$ to $C_4$ alkyl group optionally substituted, or an phenyl group optionally substituted; or $R^6$ and $R^1$, taken together, form a saturated heterocycle, optionally substituted and optionally containing an additional nitrogen or oxygen atoms, such as a 2-pyrrolidine, a 2-piperidine or a 2-morpholine.

Possible substituents of $R^1$ to $R^3$, $R^6$ and $R^7$, in particular when the groups are or contain phenyl groups or moieties, are one or two halogen, $C_1$ to $C_5$ alkoxy or polyalkyleneglycols groups, COOR, $NR_2$ or R groups wherein R is a $C_1$ to $C_4$ alkyl, or a $C_{5-6}$ cycloalkyl, aralkyl or aromatic group, the latter being also optionally substituted as defined above.

In an alternative embodiment, the ligand of formula (2-A) is a bidentate N—P ligand of general formula

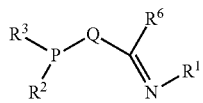

(2-E)

in which Q, $R^1$, $R^2$, $R^3$ are defined as for formula (2-B) or (2-D);

$R^6$ represents a hydrogen atom, a linear or branched $C_1$ to $C_4$ alkyl group or an phenyl group optionally substituted; or $R^6$, when taken together with $R^1$, forms a $C_3$-$C_9$ C=N function-containing heterocycle optionally substituted and optionally containing one additional nitrogen or oxygen atom.

Possible substituents of Q and $R^1$ to $R^6$, in particular when the groups are or contain phenyl groups or moieties, are one or two halogen, $CF_3$ groups or $C_1$ to $C_5$ alkoxy or polyalkyleneglycols groups, $C_1$ to $C_4$ alkyl groups, or $C_5$ to $C_{10}$ cycloalkyl, aralkyl or phenyl groups, the latter being also optionally substituted as defined above.

Alternatively one may use a complex wherein the ligand of formula (2-A') is a bidentate N—P ligand of general formula

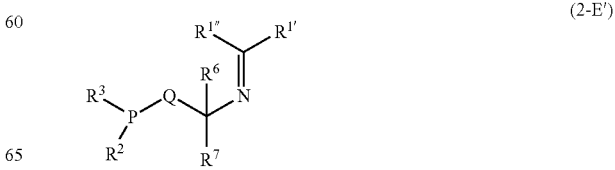

(2-E')

wherein $R^2$, $R^3$, $R^6$ and $R^7$ are as defined for (2-B) or (2-D), Q is defined as in formula (2-B); and $R^{1'}$ and $R^{1'''}$, when taken separately, represents a hydrogen atom, a linear, branched or cyclic $C_1$ to $C_6$ alkyl group optionally substituted or a phenyl group optionally substituted; or the $R^{1'}$ or $R^{1'''}$, when taken together, form a saturated ring optionally substituted, having 5 to 7 atoms and including the carbon atom to which the $R^{1'}$ and $R^{1'''}$ groups are bonded; $R^6$ and $R^{1'''}$, taken together, may form a saturated or unsaturated heterocycle, optionally substituted and optionally containing one or two additional nitrogen or oxygen atoms, containing 5 or 6 atoms and including the carbon atoms and the N atom to which the $R^6$ or $R^{1'''}$, group are bonded respectively.

Alternatively, yet in the embodiments, $R^{1'}$ and $R^{1'''}$, when taken separately, represents a hydrogen atom, a linear or branched $C_1$ to $C_4$ alkyl group optionally substituted or a phenyl group optionally substituted; or the $R^{1'}$ or $R^{1'''}$, when taken together, form a saturated ring optionally substituted, having 5 to 7 atoms and including the carbon atom to which the $R^{1'}$ and $R^{1'''}$ groups are bonded.

Possible substituents of $R^{1'}$, $R^{1'''}$, $R^2$, $R^3$, Q, $R^6$ and $R^7$, in particular when the groups are or contain phenyl groups or moieties, are one or two halogen, $CF_3$ groups or $C_1$ to $C_5$ alkoxy or polyalkyleneglycols groups, $C_1$ to $C_4$ alkyl groups, or $C_5$ to $C_{10}$ cycloalkyl, aralkyl or phenyl groups, the latter being also optionally substituted as above defined.

It is understood that, in any of the above embodiments, the ferrocenediyl, as well as the metallocenediyl above mentioned, can be in the form of a ferrocene-1,1'-diyl or of a ferrocene-1,2-diyl.

A particular embodiment of formula (2-E) is a ligand of formula (2-F), (2-F'), (2-G) or (2-G')

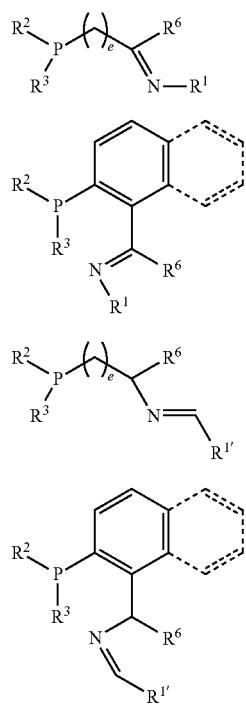

wherein the dotted lines in formula (2-G) or (2-G') indicate the presence of a phenyl or a naphthyl group; e represents 1 or 2, and in particular 1;

$R^1$, $R^2$, $R^3$, are defined as in formula (2-E), $R^{1'}$ is defined as $R^1$ in formula (2-E); and $R^6$ represents a hydrogen atom, a linear or branched $C_1$ to $C_4$ alkyl group optionally substituted, or a phenyl group optionally substituted; or $R^6$, when taken together with $R^1$, forms a $C_3$-$C_9$ C=N function-containing heterocycle optionally substituted and optionally containing one additional nitrogen or oxygen atom such as a 2-pyridyl, a 1-oxazolinyl, a 2-imidazolyl or a 2-isoquinolinyl group.

Possible substituents of $R^1$ to $R^3$ and $R^6$, in particular when the groups are or contains phenyl groups or moieties, are one or two halogen, $C_1$ to $C_5$ alkoxy or polyalkyleneglycols groups, $C_1$ to $C_4$ alkyl groups, or $C_s$ to $C_{10}$ cycloalkyl, aralkyl or phenyl groups, the latter being also optionally substituted as above defined.

In all the above embodiments when it is the that "$R^2$ and $R^3$, when taken together, may form a saturated or unsaturated ring...", one can cite a trivial example of such type of $R^2$ and $R^3$ taken together the following: diphenyl or dinaphthyl group (which will form an unsaturated atom ring) or a —$(CH_2)_5$— group (which will form a saturated 6 atom ring).

Furthermore, in all the above embodiments, a particularly appreciated mode of realization is the one where the $R^2$ and $R^3$ groups are aromatic groups optionally substituted.

In a particular embodiment of the invention the L' ligand may be a preferably $C_3$-$C_{30}$ mono-phosphine, and in particular of formula $PR^d_3$, wherein $R^d$ is a $C_1$-$C_{12}$ group, such as linear, branched or cyclic alkyl, alkoxy or aryloxy group optionally substituted, substituted or unsubstituted phenyl, diphenyl or naphthyl or di-naphthyl group, or a solvent such as THF, acetone, pyridine an $C_3$-$C_8$ ester or an $C_1$-$C_4$ alcohol. Possible substituents are those cited above for L2.

The processes of the invention are particularly attractive when are used complexes of the (2) [Ru $(L2)_2Y_2$] wherein Y represents H or Cl, and L2 represents a ligand of the formula (2-H):

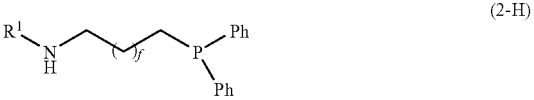

wherein $R^1$ represents a hydrogen atom or a methyl group, Ph is phenyl radical.

The ligands described above can be obtained by applying standard general methods which are well known in the state of the art and by the person skilled in the art. Therefore, their preparation does not require a specific description. For example one may revert to WO 02/22526.

In a general way, the complexes of formula (1) can be prepared and isolated prior to their use in the process according to the general methods described in the literature. A method is described in the Example.

Moreover, the complexes can be prepared in situ, by several methods, in the hydrogenation medium, without isolation or purification, just before their use.

One of the possible procedures to advantageously prepare in situ a complex of formula (1) consists in reacting an appropriate Ru complex of formula [Ru ("diene")("allyl")$_2$], wherein "diene" represents a cyclic or linear hydrocarbon containing two carbon-carbon double bonds, conjugated or not, such as for example 1,5-cyclooctadiene (COD) or norbornadiene, and "allyl" represents a linear or branched $C_3$ to $C_8$ hydrocarbon radical containing one carbon-carbon double bond such as methylallyl or allyl, with a non coordinating acid such as $HBF_4.Et_2O$, and then treating the resulting solution with the required amount of a ligands L2, and if necessary of ligand L', such as defined previously, to give a solution of a catalyst according to formula (1). Furthermore, the mixture thus obtained can also be treated with a base in the presence of a primary or secondary alcohol. Furthermore, the complexes of formula (I) can be prepared by reacting an appropriate Ru complex such as, $[RuCl_2(PPh_3)_3]$, $[RuCl_2(cod)]$ or $[RuCl_2(arene)]_2$ with the required amount of a ligands L2, and if necessary of ligand L', such as defined previously (cod representing a cyclooctadiene and arene being e.g. a benzene or naphthalene).

It is also understood that the complex of formula (I) can also be obtained in situ from complexes which have a similar formula or are cationic or anionic, for examples a complex (I) wherein Y has another meaning or a complex of formula [Ru (L2)$_2$(solvent)$_2$](Anion)$_2$, wherein the anion is a non-coordinating one, which in presence of, for example an alcohol and a base, are converted into a compound of formula (I).

To carry out the processes of the invention it is required also to use a base. The base can be the substrate itself, if the latter is basic, a corresponding alcoholate or any base having preferentially a $pK_a$ above 11. According to a particular embodiment of the invention the base may have a $pK_a$ above 14. It is also understood that preferably the base does not reduce itself a substrate of formula (I). As non-limiting examples one may cite the following type of base: alcoholate, hydroxides, alkaline or alkaline-earth carbonates, phosphazines, amides, basic alox, siliconates (i.e. silicium derivatives having SiO$^-$ or SiRO$^-$ groups), hydrides such as $NaBH_4$, NaH or KH.

One can cite, as non-limiting examples, alkaline or alkaline-earth metal carbonates, such as cesium carbonate, an alkaline or alkaline-earth metal hydroxides, $C_{1-10}$ amidures, $C_{10-26}$ phosphazine or an alcoholate of formula $(R^{13}O)_2M$ or $R^{13}OM'$, wherein M is an alkaline-earth metal, M' is an alkaline metal or an ammonium $NR^{14}_4{}^+$, $R^{13}$ stands for hydrogen or a $C_1$ to $C_6$ linear or branched alkyl radical and $R^{14}$ stands for a $C_1$ to $C_{10}$ linear or branched alkyl radical, such as sodium or potassium alcoholates. Of course, other suitable bases can be used.

According to an embodiment of the invention, the base is an alkaline alcoholate of formula $R^{13}OM'$.

As previously mentioned the processes of the invention consist in the hydrogenation of a substrate using a ruthenium complex and a base. A typical process implies the mixture of the substrate with the ruthenium complex, a base and optionally a solvent, and then treating such a mixture with molecular hydrogen at a chosen pressure and temperature.

The complexes of the invention, an essential parameter of the process, can be added to the reaction medium in a large range of concentrations. As non-limiting examples, one can cite as complex concentration values those ranging from 50 ppm to 50000 ppm, relative to the amount of substrate. Preferably, the complex concentration will be comprised between 100 and 20000 ppm. It goes without saying that the optimum concentration of complex will depend, as the person skilled in the art knows, on the nature of the latter, on the nature of the substrate and on the pressure of $H_2$ used during the process, as well as the desired time of reaction.

Useful quantities of base, added to the reaction mixture, may be comprised in a relatively large range. One can cite, as non-limiting examples, ranges between 5 to 50000 molar equivalents, relative to the complex (e.g. base/com=5 to 50000), preferably 20 to 2000, and even more preferably between 50 and 1000 molar equivalents.

The hydrogenation reaction can be carried out in the presence or absence of a solvent. When a solvent is required or used for practical reasons, then any solvent current in hydrogenation reactions can be used for the purposes of the invention. Non-limiting examples include aromatic solvents such as toluene or xylene, hydrocarbon solvents such as hexane or cyclohexane, ethers such as tetrahydrofuran or MTBE, polar solvents such as primary or secondary alcohols such as isopropanol or ethanol, or mixtures thereof. The choice of the solvent is a function of the nature of the complex and the person skilled in the art is well able to select the solvent most convenient in each case to optimize the hydrogenation reaction.

In the hydrogenation process of the invention, the reaction can be carried out at a $H_2$ pressure comprised between $10^5$ Pa and $80 \times 10^5$ Pa (1 to 80 bars) or even more if desired. Again, a person skilled in the art is well able to adjust the pressure as a function of the catalyst load and of the dilution of the substrate in the solvent. As examples, one can cite typical pressures of 1 to $50 \times 10^5$ Pa (1 to 50 bar).

The temperature at which the hydrogenation can be carried out is comprised between 0° C. and 120° C., more preferably in the range of between 50° C. and 100° C. Of course, a person skilled in the art is also able to select the preferred temperature as a function of the melting and boiling point of the starting and final products as well as the desired time of reaction or conversion. Temperatures of as high as 140° C. can be used if desired. The higher pressures of the recited pressure range are generally used with the lower temperatures of the temperature range, while the lower pressures of the recited pressure range are generally used with the higher temperatures of the temperature range. The preferred pressure and temperature conditions include a minimum temperature and pressure from the previously recited ranges to achieve a substrate conversion that is greater than 50, 75, 90 or 95% and a yield of the corresponding alcohol or diol that is greater than 40, 50, 80 or 90%. Of course, the highest conversions and yields are the most desirable, and the examples illustrate how to achieve and even exceed the previously recited values.

Furthermore, the temperature and pressure combinations that are suitable for the hydrogenation reduction of esters or lactones of the present invention are generally higher than what is required for the hydrogenation reduction of ketones. Chapter 15 of the "Handbook of Homogeneous Hydrogenation" which represents the state of the art, teaches that catalysts known to be active for hydrogenation are active only on specific types of substrates, and may not be active for other types of substrates. For example, the selectivity and unpredictability of hydrogenation is illustrated with the hydrogenation of carboxylic acid and the hydrogenation of certain carboxylic acids does not necessarily predict the successful hydrogenation of other carboxylic acid because such hydrogenation is affected by the carboxylic acid structure (See page 443, last paragraph). Similarly, the selectivity and unpredictability of hydrogenation is illustrated with the hydrogenation of esters (See Page 445, Section 15.7.2, first paragraph) and the hydrogenation of esters is subject to either an electronic effect or a chelate effect (See page 446, last paragraph and Table 15.15). The reference concludes by saying that the research efforts aimed towards active, chemoselective hydrogenation of certain C=O and C=N bonds have delivered several catalysts that approach the level of activity required for use in the synthesis of alcohols and amines. Other classes of substrates require considerable additional investigation to be conducted before homogeneous catalysts may be considered (see page 451, last paragraph). Therefore, the state of the art demonstrates the lack of predictability and teaches away from the extrapolation from one type of substrate to another without conducting considerable investigation.

In contrast, the present invention now demonstrates how to conduct processes for the reduction by hydrogenation, using molecular $H_2$, of a $C_3$-$C_{70}$ substrate containing one or two ester or lactone functional groups into their corresponding alcohols or diols. As noted, the ligands of the present invention are useful for this purpose, but the temperature and pressure conditions of the process are generally higher than what is useful for the reduction of ketones. Accordingly, prior art documents that teach how to reduce ketone substrates are non-analogous art to the processes of the present invention.

EXAMPLES

The invention will now be described in further detail by way of the following examples, wherein the temperatures are indicated in degrees centigrade and the abbreviations have the usual meaning in the art.

All the procedures described hereafter have been carried out under an inert atmosphere unless stated otherwise. Hydrogenations were carried out in open glass tubes placed inside a stainless steel autoclave. $H_2$ gas (99.99990%) was used as received. All substrates and solvents were distilled from appropriate drying agents under Ar. NMR spectra were recorded on a Bruker AM-400 ($^1H$ at 400.1 MHz, $^{13}C$ at 100.6 MHz, and $^{31}P$ at 161.9 MHz) spectrometer and normally measured at 300 K, in $CDCl_3$ unless indicated otherwise. Chemical shifts are listed in ppm.

Example 1

A) Preparation of complexes [$RuCl_2$(L-1)$_n$], [$RuCl_2$(L-2)$_2$], [$RuCl_2$(L-4)$_2$]

a) Preparation of the Complex Dichloro bis[2-(Diphenylphosphino)ethylamine]Ruthenium ([$RuCl_2$(L-1)$_2$])

Under argon, a round-bottomed Schlenck flask, equipped with a magnetic stirring bar, was charged with $RuCl_2(PPh_3)_3$ (418.6 mg, 0.436 mmol) and toluene (6 mL) Then under stirring, a solution of 2-(diphenylphosphino)ethylamine (201.6 mg, 0.879 mmol) in toluene (3 mL) was added, more toluene (3 mL) was added to rinse. Then the dark-brown solution was heated in an oil bath at 100° C. for six hours. The resulting yellow suspension was cooled to room temperature, and filtered under argon. The yellow solid was rinsed with toluene until the filtrate was colourless and then dried in-vacuo. The desired complex (258.4 mg, 0.41 mmol, 94%) was then collected as a pale-yellow solid. $^{31}P\{^1H\}$-NMR analysis showed the presence of two species the major one being the trans-chloride-cis-phosphorous complex (75%) and the minor one being the cis-chloride-cis-phosphorous complex (25%).

$^1H$-NMR ($CD_2Cl_2$): δ (A) 7.24 (m, 4H), 7.16 (m, 8H), 7.07 (m, 8H), 3.78 (brs, 4H, $NH_2$), 3.22 (m, 4H), 2.70 (brs, 4H).

$^{13}C\{^1H\}$-NMR ($CD_2Cl_2$): δ (A) 137.1 (Carom), 133.9 (t, J=5 Hz, CHarom), 129.2 (CHarom), 127.6 (t, J=5 Hz, CHarom), 41.9 ($CH_2$), 33.3 (t, J=13.5 Hz, $CH_2$).

$^{31}P\{^1H\}$-NMR ($CD_2Cl_2$): A (75%) δ=62.6 ppm (s); B (25%) δ=67.5 ppm (d, J=32 Hz), 56.2 ppm (d, J=32 Hz).

b) Preparation of the Complex Dichloro [2-(Diphenylphosphino) ethylamine][triphenylphosphine]Ruthenium ([$RuCl_2$(L-1)($PPh_3$)])

Under argon, a round-bottomed Schlenck flask, equipped with a magnetic stirring bar, was charged with $RuCl_2(PPh_3)_3$ (20.0 g, 20.9 mmol) and THF (160 mL). Then under stirring, neat 2-(diphenylphosphino)ethylamine (4.83 g, 21.1 mmol) was added over five minutes. Next, the reaction mixture was stirred at room temperature for three hours. During that time, the dark ruthenium suspension quickly dissolves before precipitating back as a pink solid. Reaction mixture was then filtered under nitrogen (dark filtrate). The obtained solid was washed with THF (3×40 ml) and then MTBE. The pink solid was then dried in-vacuo overnight to afford the ruthenium complex as a pink solid (14.0 g, 21 mmol).

$^{31}P\{^1H\}$-NMR analysis showed the presence of several ruthenium species, and also showed the presence of free triphenylphosphine probably liberated by product evolution in solution, as the solid was washed several times with THF.

$^{31}P\{^1\}$-NMR ($CD_2Cl_2$): δ=59.96 (d, J=30.7 Hz), 59.46 (t, J=35.1 Hz), 58.51 (s), 44.64 (d, J=30.7 Hz), 44.29 (d, J=30.7 Hz), −4.84 (s, free $PPh_3$).

c) Preparation of the Complex Dichloro bis[3-(Diphenylphosphino)-1-propylamine]Ruthenium ([$RuCl_2$(L-2)$_2$])

Under argon, a round-bottomed Schlenck flask, equipped with a magnetic stirring bar, was charged with $RuCl_2(PPh_3)_3$ (1.028 g, 1.07 mmol) and with a solution of 3-(diphenylphosphino)-1-propylamine (566.8 mg, 2.33 mmol) in toluene (5 mL) More toluene (5 mL) was added to rinse. Then the dark-brown solution was heated in an oil bath at 100° C. for 16 h. The resulting brick-orange suspension was cooled to room temperature, and added to pentane (50 mL) with stirring. The yellow solid was collected by filtration, washed with pentane (2×3 mL) and dried in vacuo to provide the desired complex (672.6 mg, 1.02 mmol, 95%) as a yellow-mustard solid. $^{31}P\{^1H\}$-NMR analysis showed the presence of two species.

$^1H$-NMR ($CD_2Cl_2$): δ (A) 7.19 (t, J=7.2 Hz, 4H), 7.14 (m, 8H), 7.05 (t, J=7.2 Hz, 8H), 3.28 (brs, 4H), 3.02 (brs, 4H), 2.66 (m, 4H), 2.0 (m, 4H).

$^{13}C$-NMR ($CD_2Cl_2$): δ (A) 138.4 (t, J=19.2 Hz, Carom), 134.2 (t, J=4.8 Hz, CHarom), 129.0 (CHarom), 127.5 (t, J=4.8 Hz, CHarom), 41.3 ($CH_2$), 26.9 (t, J=13.6 Hz, $CH_2$), 24.7 ($CH_2$).

$^{31}P\{^1H\}$-NMR ($CD_2Cl_2$): A (82%) δ=33.5 ppm (s), B (18%) δ=49.8 ppm (s).

d) Preparation of the Complex Dichloro bis-2-[2-(diisobutylphosphino)ethyl]pyridine Ruthenium ([$RuCl_2$(L-4)$_2$])

Under argon, a round-bottomed Schlenck flask, equipped with a magnetic stirring bar, was charged with $RuCl_2(PPh_3)_3$ (535.2 mg, 0.56 mmol) and with a solution of 2-[2-(diisobutylphosphino)ethyl]pyridine (306.5 mg, 1.22 mmol) in toluene (3 mL). More toluene (2×1 mL) was added to rinse. Then the dark-brown solution was heated in an oil bath at 100° C. for 6 h. The resulting red solution was cooled to room temperature, and the solvent removed in vacuo to give an orange solid. The solid was dissolved in $CH_2Cl_2$ (3 mL), MeOH (15 mL) was added and the solution was concentrated in vacuo until a yellow precipitate forms. The solid was recovered by filtration, washed with MeOH (1 mL) and dried in vacuo to give the desired complex (458.9 mg). $^{31}P\{^1H\}$-NMR analysis showed the presence of free $PPh_3$ (44 wt %). The solid (425.8 mg) was dissolved in $CH_2Cl_2$ (10 mL), and the solution added to a suspension of CuCl (86.1 mg, 0.87 mmol) in $CH_2Cl_2$ (10 mL). More $CH_2Cl_2$ (5 mL) was added to rinse.

The solution was stirred for 5 min. and then the solvent was removed in vacuo. The resulting solid was triturated with a mixture of hexane (25 mL)/CH$_2$Cl$_2$ (5 mL) and then filtered over a pad of Celite. The pad was further washed with hexane/CH$_2$Cl$_2$ (5/1, 3×5 mL). The combined filtrate was concentrated in vacuo until precipitation of a yellow solid occurred. The solid was recovered by filtration and dried in vacuo to give the desired complex (152.1 mg, 0.22 mmol, 40%) as a yellow solid, free of triphenylphosphine.

$^1$H-NMR (CD$_2$Cl$_2$): δ 8.18 (d, J=5.9 Hz, 1H), 7.69 (ddd, J=1.5, 7.2, 7.7 Hz, 1H), 7.2 (d, J=7.2 Hz, 1H), 6.84 (ddd, J=1.5, 5.9, 7.2 Hz, 1H), 4.5 (brs, 1H), 2.9 (brs, 1H), 2.5 (brs, 1H), 2.3 (brs, 2H), 2.1 (brs, 1H), 1.99 (brs, 1H), 1.68 (brd, J=14 Hz, 2H), 1.55 (brs, 1H), 0.8-1.2 (brm, 12H).

$^{13}$C-NMR (CD$_2$Cl$_2$): δ 167.6 (Carom), 158.5 (CHarom), 136.9 (CHarom), 124.2 (CHarom), 121.5 (CHarom), 40.0 (brs, CH$_2$), 36.6 (brs, CH$_2$), 33.2 (CH$_2$), 26.1 (CH$_3$), 25.7 (CH$_3$), 25.3 (CH), 19.7 (t, J=10.4 Hz, CH$_2$).

$^{31}$P{$^1$H}-NMR (CD$_2$Cl$_2$): δ=40.2 ppm (s).

B) Preparation of imino-phosphine ligands (L-6 to L-10)

a) Preparation of N-[2-(diphenylphosphino)ethyl]-N-[phenylmethylene]amine (L-6)

Under argon, a solution of 2-diphenylphosphino-ethylamine (590.3 mg, 2.57 mmol) and benzaldehyde (275.0 mg, 2.59 mmol) in ethanol (15 mL) was heated at 65° C. (oil bath) for 4 h. Then, the solvent was removed in-vacuo to give the desired product (>98% by $^1$H-NMR) as a colourless oil which solidified on standing (733.9 mg, 2.31 mmol, 90%).

$^1$H-NMR (CD$_2$Cl$_2$): δ 8.2 (s, 1H, CH=N), 7.68-7.62 (m, 2H), 7.49-7.43 (m, 4H), 7.4-7.28 (m, 9H), 3.71 (ddt, J=1, 8, 9 Hz, 2H), 2.45 (ap t, J=8 Hz, 2H).

$^{13}$C-NMR (CD$_2$Cl$_2$): δ 161.3 (CH C=N), 139.2 (d, J=12.9 Hz, Carom), 136.7 (Carom), 133.1 (d, J=18.6 Hz, CHarom), 130.9 (CHarom), 128.91 (CHarom), 128.86 (CHarom), 128.8 (d, J=6.5 Hz, CHarom), 128.4 (CHarom), 58.7 (d, J=21 Hz, CH$_2$), 30.1 (d, J=12.9 Hz, CH$_2$).

$^{31}$P{$^1$H}-NMR (CD$_2$Cl$_2$): δ=-18.5 ppm (s).

b) Preparation of N-[(3,5-Dimethylphenyl)methylene]-N-[2-(diphenylphosphino) ethyl]amine (L-7)

Under Argon, a Solution of 2-Diphenylphosphino-Ethylamine (652.2 Mg, 2.84 Mmol) and 3,5-dimethyl-benzaldehyde (387.4 mg, 2.89 mmol) in ethanol (15 mL) was heated at 65° C. (oil bath) for 4 h. Then, the solvent was removed in-vacuo to give the desired product (>98% by $^1$H-NMR) as a colourless oil (993.2 mg, 2.8 mmol, quantitative).

$^1$H-NMR (CD$_2$Cl$_2$): δ 8.13 (s, 1H, CH=N), 7.48-7.42 (m, 4H), 7.35-7.29 (m, 6H), 7.25 (s, 2H), 7.04 (s, 1H), 3.68 (dq, J=1.3, 7.7 Hz, 2H), 2.44 (t, J=7.7 Hz, 2H), 2.3 (s, 6H).

$^{13}$C-NMR (CD$_2$Cl$_2$): δ 161.7 (CH C=N), 139.2 (d, J=13.7 arom), 138.5 (Carom), 136.6 (Carom), 133.1 (d, J=19.4 Harom), 132.6 (CHarom), 128.9 (CHarom), 128.8 (d, J=6.5 CHarom), 126.2 (CHarom), 58.7 (d, J=21 Hz, CH$_2$), 30.2 (d, J=12.9 Hz, CH$_2$), 21.2 (CH$_3$).

$^{31}$P{$^1$H}-NMR (CD$_2$Cl$_2$): δ=-18.5 ppm (s).

c) Preparation of N-[cyclohexylmethylene]-N-[2-(diphenylphosphino)ethyl]amine (L-8)

Under argon, a solution of 2-diphenylphosphino-ethylamine (619.0 mg, 2.7 mmol) and cyclohexane carbaldehyde (306.2 mg, 2.73 mmol) in ethanol (15 mL) was heated at 65° C. (oil bath) for 4 h. Then, the solvent was removed in-vacuo to give the desired product (>98% by $^1$H-NMR) as a colourless liquid (880.5 mg, 2.7 mmol, quantitative).

$^1$H-NMR (CD$_2$Cl$_2$): δ 7.47-7.39 (m, 5H), 7.35-7.28 (m, 6H), 3.42 (q, J=8.2 Hz, 2H), 2.32 (t, J=7.7 Hz, 2H), 2.12-2.01 (m, 1H), 1.77-1.67 (m, 4H), 1.67-1.58 (m, 1H), 1.34-1.1 (5H)

$^{13}$C-NMR (CD$_2$Cl$_2$): δ 169.2 (CH=N), 139.2 (d, J=13.7 Hz, Carom), 133.1 (d, J=19.4 Hz, CHarom), 128.9 (CHarom), 128.8 (d, J=6.5 Hz, CHarom), 58.5 (d, J=20.2 Hz, CH$_2$), 43.6 (CH), 30.2 (d, J=12.1 Hz, CH$_2$), 29.9 (CH$_2$), 36.5 (CH$_2$), 25.9 (CH$_2$).

$^{31}$P{$^1$H}-NMR (CD$_2$Cl$_2$): δ=-18.9 ppm (s).

d) Preparation of N-benzylidene-N-[3-(diphenylphosphino)propyl]amine (L-9)

Under argon, a solution of 3-diphenylphosphino-propylamine (631.2 mg, 2.6 mmol) and benzaldehyde (278.1 mg, 2.6 mmol) in ethanol (15 mL) was heated at 65° C. (oil bath) for 4 h. Then, the solvent was removed in-vacuo to give the desired product (>98% by $^1$H-NMR) as a white solid (822.3 mg, 2.5 mmol, 96%).

$^1$H-NMR (CD$_2$Cl$_2$): δ 8.24 (s, CH=N), 7.72-7.68 (m, 2H), 7.45-7.37 (m, 7H), 7.33-7.28 (m, 6H), 3.66 (dt, J=1.0, 6.7 Hz, 2H), 2.13 (dd, J=5.4, 7.9, 10.5 Hz, 2H), 1.85-1.75 (m, 2H).

$^{13}$C-NMR (CD$_2$Cl$_2$): δ 161.3 (CH C=N), 139.9 (d, J=13.7 Hz, Carom), 136.9 (Carom), 133.1 (d, J=18.6 Hz, CHarom), 130.8 (CHarom), 128.9 (CHarom), 128.8 (CHarom), 128.7 (d, J=6.5 Hz, CHarom), 128.4 (CHarom), 62.5 (d, J=12.9 Hz, CH$_2$), 27.8 (d, J=16.9 Hz, CH$_2$), 25.8 (d, J=11.3 Hz, CH$_2$).

$^{31}$P{$^1$H}-NMR (CD$_2$Cl$_2$): δ=-15.9 ppm (s).

e) Preparation of N-benzylidene-N-[3-(diisobutylphosphino)propyl]amine (L-10)

Under argon, a solution of 3-diisobutylphosphino-propylamine (428.5 mg, 2.11 mmol) and benzaldehyde (226.9 mg, 2.14 mmol) in ethanol (15 mL) was heated at 65° C. (oil bath) for 4 h. Then, the solvent was removed in-vacuo to give the desired product (>98% by $^1$H-NMR) as a colourless liquid (614.1 mg, 2.1 mmol, quantitative).

$^1$H-NMR (CD$_2$Cl$_2$): δ 8.27 (s, 1H), 7.73-7.68 (m, 2H), 7.43-7.38 (m, 3H), 3.63 (t, J=6.7 Hz, 2H), 1.82-1.74 (m, 2H), 1.73-1.64 (m, 2H), 1.41-1.37 (m, 2H), 1.35-1.22 (m, 4H), 0.98 (d, J=6.7 Hz, 6H), 0.97 (d, J=6.7 Hz, 6H).

$^{13}$C-NMR (CD$_2$Cl$_2$): δ 160.9 (CH C=N), 136.9 (Carom), 130.7 (CHarom), 128.9 (CHarom), 128.3 (CHarom), 63.1 (d, J=11.3 Hz, CH$_2$), 39.5 (d, J=13.7 Hz, CH$_2$), 27.7 (d, J=12.9 Hz, CH$_2$), 26.9 (d, J=13.7 Hz, CH$_2$), 26.7 (d, J=12.9 Hz, CH$_2$), 24.53 (d, J=8.9 Hz, CH$_3$), 24.45 (d, J=8.1 Hz, CH$_3$).

$^{31}$P{$^1$H}-NMR (CD$_2$Cl$_2$): δ=-39.6 ppm (s).

The structure of the ligands is reported in Table 1:

TABLE 1

Structure of ligands (L-1 to L-10) used in complexes of formula (1)

| structure | name |
|---|---|
| H$_2$N∼∼PPh$_2$ | L-1 |
| H$_2$N∼∼∼PPh$_2$ | L-2 |

TABLE 1-continued

Structure of ligands (L-1 to L-10) used in complexes of formula (1)

| structure | name |
|---|---|
| H₂N–CH₂CH₂CH₂–P(iBu)₂ | L-3 |
| 2-(pyridyl)ethyl–P(iBu)₂ | L-4 |
| 2-(PPh₂)C₆H₄–CH=N–CH₂Ph | L-5 |
| Ph–CH=N–CH₂CH₂–PPh₂ | L-6 |
| 3,5-Me₂C₆H₃–CH=N–CH₂CH₂–PPh₂ | L-7 |
| Cy–CH=N–CH₂CH₂–PPh₂ | L-8 |
| Ph–CH=N–CH₂CH₂CH₂–PPh₂ | L-9 |
| Ph–CH=N–CH₂CH₂CH₂–P(iBu)₂ | L-10 |

Ligands L-1 and L-2 are commercially available (Fluka). Ligands L-3 and L-4 were prepared according to Rautenstrauch, V. et al. in WO 02/22526 A2.

C) Preparation of complexes [RuCl$_2$(L-6 to L-10)$_2$]

See below example 2b) for the in-situ generation of these complexes.

Example 2

Catalytic Hydrogenation of Various Esters Using Complexes of Formula (1)

a) using pre formed complex

A typical catalytic hydrogenation using RuCl$_2$(L-1)$_2$ as pre-catalyst is described below with methyl benzoate as substrate:

Under argon, a solution of methyl benzoate (3.249 g, 24 mmol) in THF (2 mL) was added with a syringe, followed by more THF (2×1 mL), to a Keim autoclave equipped with a glass liner containing [RuCl$_2$(L-1)$_2$] (7.5 mg, 0.012 mmol, 0.05 mol %), solid NaOMe (128.2 mg, 2.4 mmol, 10 mol %) and THF (12.5 mL) The autoclave was pressurised with hydrogen gas at 50 bars and placed in a thermostatted oil bath set at 100° C. After 2 h 30 min, the autoclave was removed from the oil bath, and cooled in a cold-water bath. Then, the reaction mixture was diluted with citric acid 10% w/w (25 mL) and extracted with MTBE (100 mL). The organic phases was washed with aq. sat. NaCl (3×50 mL). Gas chromatography after silylation showed the following products: benzyl alcohol (97.5%), benzoic acid (2.5%). Then, the organic phase was washed successively with aq. KOH 1 M (50 mL) and aq. sat. NaCl (3×50 mL), and dried over MgSO$_4$ anh. Filtration and removal of the solvent in vacuo gave a yellow liquid (3.486 g). Purification by Kugelrohr distillation (130-140° C./8.5 mbar) gave pure benzyl alcohol (2.081 g, 19 mmol, 80%) as a colourless liquid.

$^1$H NMR (CDCl$_3$, 400 MHz): δ 7.38-7.25 (m, 5H), 4.65 (s, 2H), 2.02 (s, 1H).

$^{13}$C NMR (CDCL$_3$, 100 MHz): δ 140.9 (s), 128.6 (d), 127.6 (d), 126.9 (d), 62.3 (t).

b) using in-situ formed complex

A typical catalytic hydrogenation using in-situ formed RuCl$_2$(L-6)$_2$ as pre-catalyst is described below for methyl benzoate as substrate:

Under argon, a solution of methyl benzoate (2.729 g, 20 mmol) in THF (2 mL) was added with a syringe, followed by more THF (2×1 mL), to a Keim autoclave equipped with a glass liner containing [RuCl$_2$(para-cymene)]$_2$ (6.9 mg, 0.01 mmol, 0.05 mol %), ligand L-6 (15.4 mg, 0.05 mmol, 0.24 mol %), solid NaOMe (106.2 mg, 2 mmol, 10 mol %) and THF (6 mL). Then a solution of tridecane (338.1 mg, 1.83 mmol), as internal standard, is added in THF (2 mL), followed by more THF (2×1 mL). The autoclave was then pressurised with hydrogen gas at 50 bars and placed in a thermostatted oil bath set at 100° C. After 1 h, the autoclave was removed from the oil bath, and cooled in a cold-water bath. An aliquot (0.3 mL) was withdrawn and diluted with MTBE (5 mL). The organic phase was washed with aq. sat. NaCl (5 mL), filtered through Celite and analysed. GC yield based on the internal standard gave the yield of 81% in benzyl alcohol.

Using methyl benzoate as a test substrate several complexes with ligands described in Table 1, bases and solvent were tested under these conditions. The resulted are summarized in Table 2.

TABLE 2

Hydrogenation of methyl benzoate using [RuCl$_2$(L)n]

| Test | Complex | Com/Base | Base | Solvent | Conv. |
|---|---|---|---|---|---|
| 1 | [RuCl$_2$(PPh$_3$)$_3$] | 4000/1000000 | NaOMe | THF | 0 |
| 2 | [(RuCl$_2$(Cym))$_2$] | 500/100000 | NaOMe | THF | 0 |
| 3 | [RuCl$_2$(L-1)$_2$] | 1000/1000000 | NaOMe | THF | 0[1] |
| 4 | [RuCl$_2$(L-1)$_2$] | 1000/1000000 | NaOMe | THF | 86 |
| 5 | [RuCl$_2$(L-1)$_2$] | 1000/100000 | NaOMe | THF | 97 |
| 6 | [RuCl$_2$(L-1)$_2$] | 1000/100000 | NaOMe | THF | 98[2] |
| 7 | [RuCl$_2$(L-1)$_2$] | 500/100000 | NaOMe | THF | 98 (81)[3a] |
| 8 | [RuCl$_2$(L-1)$_2$] | 1000/100000 | NaOMe | THF | 75[4] |
| 9 | [RuCl$_2$(L-1)$_2$] | 1000/100000 | NaOMe | THF | 93[5] |
| 10 | [RuCl$_2$(L-1)$_2$] | 2000/100000 | NaOMe | THF | 32[6] |
| 11 | [RuCl$_2$(L-1)$_2$] | 1000/1000000 | NaOMe | MTBE | 87 |
| 12 | [RuCl$_2$(L-1)$_2$] | 1000/1000000 | NaOMe | Toluene | 87 |
| 13 | [RuCl$_2$(L-1)$_2$] | 1000/1000000 | NaOMe | $^i$PrOH | 87 |
| 14 | [RuCl$_2$(L-1)$_2$] | 1000/1000000 | NaOMe | EtOH | 87 |
| 15 | [RuCl$_2$(L-1)$_2$] | 1000/1000000 | NaOMe | MeOH | 20 |
| 16 | [RuCl$_2$(L-1)$_2$] | 1000/1000000 | NaOEt | THF | 83 |
| 17 | [RuCl$_2$(L-1)$_2$] | 1000/1000000 | NaO$^t$Bu | THF | 96 (85)[7] |
| 18 | [RuCl$_2$(L-1)$_2$] | 1000/1000000 | NaOH | THF | 49 |
| 19 | [RuCl$_2$(L-1)$_2$] | 5000/1000000 | NaHMDS[8] | THF | 23[9] |
| 20 | [RuCl$_2$(L-1)(PPh$_3$)] | 1000/1000000 | NaOMe | THF | 22 |
| 21 | [RuCl$_2$(L-2)$_2$] | 1000/1000000 | NaOMe | THF | 70 |
| 22 | [RuCl$_2$(L-2)$_2$] | 1000/100000 | NaOMe | THF | 54[2] |
| 23 | [RuCl$_2$(L-3)$_2$] | 500/100000 | NaOMe | THF | 6[2] |
| 24 | [RuCl$_2$(L-4)$_2$] | 500/100000 | NaOMe | THF | 7[3] |
| 25 | [RuCl$_2$(L-5)$_2$] | 500/100000 | NaOMe | THF | 31[2] |
| 27 | [RuCl$_2$(L-6)$_2$] | 500/100000 | NaOMe | THF | 81[2] |
| 28 | [RuCl$_2$(L-7)$_2$] | 500/100000 | NaOMe | THF | 91[2] |
| 29 | [RuCl$_2$(L-8)$_2$] | 500/100000 | NaOMe | THF | 82[2] |
| 30 | [RuCl$_2$(L-9)$_2$] | 500/100000 | NaOMe | THF | 11[2] |
| 31 | [RuCl$_2$(L-10)$_2$] | 500/100000 | NaOMe | THF | 8[2] |

Com/Base: molar ratio in ppm relative to the substrate.
Conv. = conversion (in %, analysed by GC) of methyl benzoate into benzyl alcohol after 1 hour. Reaction conditions: H$_2$ gas (50 bars), 100° C., solvent (1.4 M).
[1] Test performed under an atmosphere of argon.
[2] Catalyst generated in-situ with L (0.22 mol %) and [(RuCl$_2$(Cym))$_2$] (0.05 mol %). Indicated is GC yield based on internal standard.
[3] Test performed during 2 h 30 min; [a] isolated yield in brackets; [b] indicated is GC yield based on internal standard.
[4] Test performed at 50° C.
[5] Test performed under H$_2$ gas of 20 bars.
[6] Test performed under H$_2$ gas of 10 bars. GC yield based on internal standard in brackets.
[7] Isolated yield in brackets.
[8] NaHMDS: Sodium bis(trimethylsilyl)amide.
[9] Test performed during 2 hours.

Several others esters (see Table 3) were hydrogenated under identical conditions as reported in Table 4 with RuCl$_2$(L-1)$_2$. The reaction conditions were identical to those reported above for methyl benzoate.

| | Structure and name of substrates used | |
|---|---|---|
| Substrate | Structure | Name |
| 1 | | Methyl benzoate |
| 2 | | Butyl benzoate |

-continued

| Substrate | Structure and name of substrates used | |
|---|---|---|
| | Structure | Name |
| 3 | | iso-Propyl benzoate |
| 4 | | tert-Butyl benzoate |
| 5 | | Methyl 4-methylbenzoate |
| 6 | | Methyl 4-methoxybenzoate |
| 7 | | Methyl 4-(dimethylamino)benzoate |
| 8 | | Methyl 4-chlorobenzoate |
| 9 | | Mehyl 4-(trifluoromethyl)benzoate |
| 10 | | Methyl 3-(dimethylamino)benzoate |
| 11 | | Methyl phenylacetate |

-continued

| Substrate | Structure | Name |
|---|---|---|
| 12 | 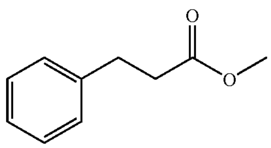 | Methyl 3-phenylpropanoate |
| 13 | 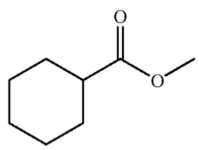 | Methyl cyclohexanecarboxylate |
| 14 | 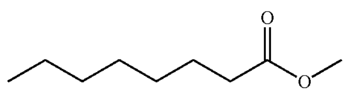 | Methyl octanoate |
| 15 | 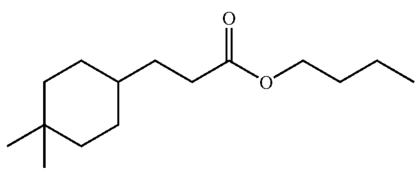 [SMILES: CCCCOC(=O)CCC1CCC(C)(C)CC1] | Butyl 3-(4,4-dimethylcyclohexyl) propanoate |
| 16 | 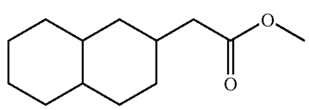 | Methyl perhydro-2-naphthylacetate |
| 17 | 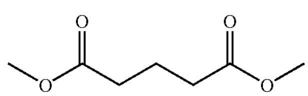 | Dimethyl pentanedioate |
| 18 | 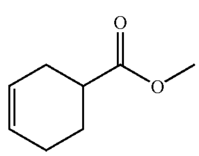 | Methyl 3-cyclohexene-1-carboxylate |
| 19 | 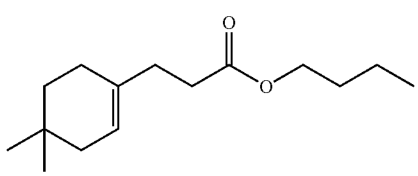 [SMILES: CCCCOC(=O)CCC1=CCC(C)(C)CC1] | Butyl 3-(4,4-Dimethyl-1-cyclohexen-1-yl) propanoate |
| 20 | 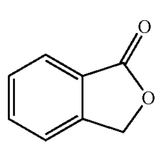 | 3H-Benzo[c]furan-1-one |
| 21 | 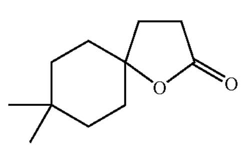 | 8,8-Dimethyl-1-oxaspiro[4.5]decan-2-one |

-continued

| Substrate | Structure | Name |
|---|---|---|
| 22 | 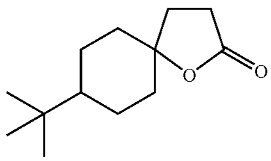 | 8-tert-Butyl-1-oxa-spiro[4.5]decan-2-one |
| 23 | 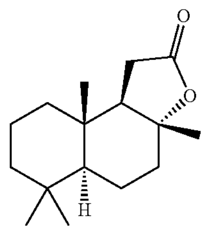 [SMILES: CC1(C)CCC[C@]2(C)[C@H]3CC(=O)O[C@]3(C)CC[C@@H]12] | 8,12-Epoxy-13,14,15,16-tetranorlabdan-12-one (Sclareolide) |
| 24 | 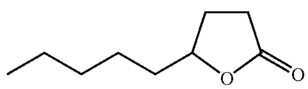 | 5-Pentyl-dihydro-furan-2-one |
| 25 | 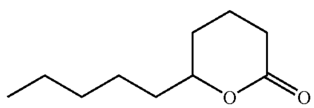 | 6-Pentyl-tetrahydro-pyran-2-one |

TABLE 4

Results obtained using the general conditions described above

| Test | Substrate (Table 3) | Conversion (%) | Isolated yield (%) |
|---|---|---|---|
| 1 | 1 | 98 | 81 |
| 2 | 2 | 98 | 85 |
| 3 | 3 | 97 | 79 |
| 4 | 4 | 98 | 78 |
| 5 | 5 | 97 | 93 |
| 6 | 6 | 94 | 75 |
| 7 | 7 | 93 | 77[1] |
| 8 | 8 | 88 | 67 |
| 9 | 9 | 72 | 46 |
| 10 | 10 | 99 | 92 |
| 11 | 11 | 98 | 82 |
| 12 | 12 | 56 | 37 |
| 13 | 13 | 94 | 82 |
| 14 | 14 | 86 | 75 |
| 15 | 15 | 56 | 45[2] |
| 16 | 16 | 97 | 82[3] |
| 17 | 17 | 94 | 72 |
| 18 | 18 | 71 | 59[4] |
| 19 | 19 | 81 | 80[1] |
| 20 | 19 | 93 | 90[2] |
| 21 | 20 | 97 | 76 |
| 22 | 21 | 79 | 56[4] |
| 23 | 22 | 75 | 68[4] |
| 24 | 23 | 97 | 91[5] |
| 25 | 24 | 98 | 91[6] |
| 26 | 25 | 98 | 93[6] |

Conversion: (in %, analysed by GC after silylation) of ester to alcohol after 2 h 30 min.
Reaction conditions: Substrate (20 mmol), $H_2$ gas (50 bars), $RuCl_2(L-1)_2$ 0.05 mol %, NaOMe 10 mol %, THF (14 mL) at 100° C. during 2 h 30 min.
[1] Reaction run for 4 h.
[2] Reaction run with KOMe (10 mol %) in THF during 5 h at 100° C. with $H_2$ gas (30 bars).
[3] Reaction run for 6 h.
[4] Reaction run with S/C = 1000 and S/B = 1 during 1 h at 100° C. with $H_2$ gas (50 bars).
[5] Reaction run with KOMe (10 mol %) in toluene during 6 h at 100° C. with $H_2$ gas (30 bars).
[6] Reaction run with KOMe (10 mol %) in toluene during 4 h at 100° C. with $H_2$ gas (50 bars).

Example 3

Useful Temperature and Pressure Combinations

Different conditions are illustrated for the hydrogenation reduction reaction of methyl benzoate to benzyl alcohol catalysed by the following ligand:

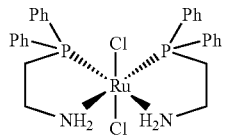

The methyl benzoate concentration is 20 mmol, the complex concentration is 0.01 mmol, a base of NaOMe is used at a concentration of 1 mmol, with 10 mL of the solvent THF. The pressure was varied from 10 to 70 bar of hydrogen at 20 C, while the temperature was varied from 60° C. to 140° C. and the reaction conducted for a period of 1 to 4 hr. for various tests.

With the temperature held at 100° C., the pressures were varied from 10 to 70 bar, with GC yields of >99% achieved at 50 and 70 bar, and no variation of the H2 consumption rate. At 50 bar, the reaction proceeded rapidly and a 78% GC yield was obtained after even 15 min. At 30 bar, H2 consumption was slower, but a GC yield of 96% was achieved after 1 hour. At 10 bar, the GC yield dropped significantly and a GC yield of 47% was obtained after 4 hr.

Variations of temperature showed a more dramatic effect on hydrogen consumption rate than initial hydrogen pressure. At a pressure of 50 bar hydrogen, as the reaction temperature was varied from 60° C. to 140° C., the reaction rate steadily increased. At 100° C. the GC yield was quantitative, and the reaction was complete when hydrogen pressure reaches a constant value. Therefore, the time to reach half conversion, which corresponds to half the hydrogen pressure drop, can be approximated as about 40 min, 20 min, 10 min and 5 min for a temperature of 60° C., 80° C., 100° C. and 140° C. respectively. From 80° C. to 140° C., GC yields of 99% were obtained after 1 hr, whereas at 60° C. a reaction time of 2 hr was necessary to reach a GC yield of 90%.

Example 4

Comparative Tests

The following tests show that ligands that are effective in the reduction reaction of esters and lactones do not work in the same way for the reduction of amides. The hydrogenation of two amides, namely azepan-1-yl(phenyl)methanone and 1-(azepan-1-yl)-3-methylbutan-1-one, was carried out in the presence of 0.05 mol % $RuCl_2((Ph)_2PCH_2CH_2NH_2)_2$, 5 mol % NaOMe, $H_2$ gas (50 bar) and THF at 100° C. for an hour.

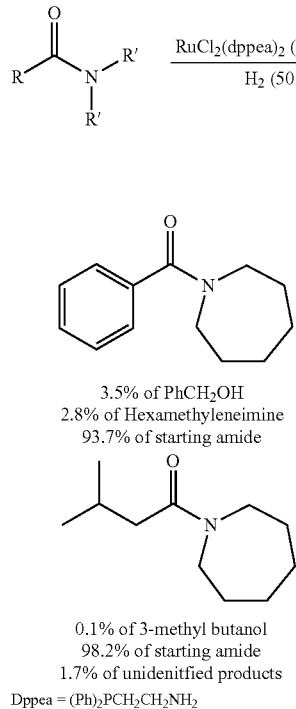

Dppea = $(Ph)_2PCH_2CH_2NH_2$

As shown in the diagram above, no amine was produced in the reaction of 1-(azepan-1-yl)-3-methylbutan-1-one, and only less than 3% of amine was produced in the reaction with azepan-1-yl(phenyl)methanone as the starting amide. The by-products of very small amounts of alcohols come from a side reduction, i.e., hydrolysis of the amide by the basis (alcoholate) and the reduction of the resulting esters. This shows that the reduction of amides provides such a minimal yield that it is practically and commercially useless.

What is claimed is:

1. A process for the reduction by hydrogenation, using molecular $H_2$, of a $C_3$-$C_{70}$ substrate containing one or two ester or lactone functional groups into its corresponding alcohol or diol, which comprises carrying out the process under suitable pressure and temperature conditions in the presence of a base and at least one complex in the form of a ruthenium complex of formula $$[Ru(L2)_b(L')_aY_2] \quad (1)$$

wherein L2 represents a $C_4$-$C_{40}$ bidentate ligand wherein the coordinating groups consist of one amino or imino group and one phosphino group;
L' represents a $C_3$-$C_{70}$ mono-phosphine or a solvent;
b is 1 and a is 1 or 2 or b is 2 and a is 0; and
each Y represents, simultaneously or independently, CO, a hydrogen or halogen atom, a hydroxyl group, a $BH_4$ or $AlH_4$ group or a $C_1$-$C_6$ alkoxy or carboxylic radical.

2. The process according to claim 1, wherein the amino group is a $NH_2$ or NH group.

3. The process according to claim 1, wherein the ruthenium complex is of formula $$[Ru(L2)_2Y_2] \quad (2)$$

wherein L2 and Y have the meaning indicated in claim 1.

4. The process according to claim 1, wherein L2 is a compound of one of the formulae

(2-A)

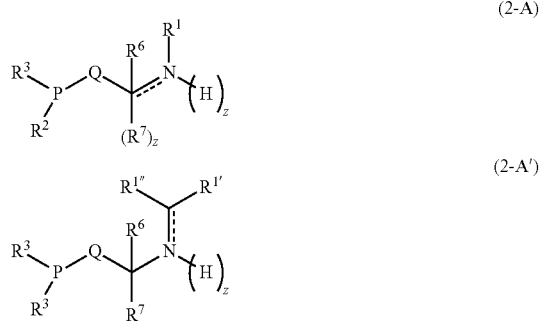
(2-A')

wherein the dotted line indicates a single or double bond;
z is 0 or 1 when the carbon-nitrogen bond with the dotted line represents a single or double bond respectively;
$R^1$ represents a hydrogen atom, a linear, branched or cyclic $C_1$ to $C_{10}$ alkyl or alkenyl group optionally substituted;
$R^{1'}$ and $R^{1'''}$, when taken separately, represents a hydrogen atom, a linear, branched or cyclic $C_1$ to $C_9$ alkyl or alkenyl group optionally substituted or a $C_6$ to $C_{10}$ aromatic group optionally substituted; the $R^{1'}$ or $R^{1'''}$, when taken together, form a saturated or unsaturated ring optionally substituted, having 5 to 12 atoms and including the carbon atom to which the $R^{1'}$ and $R^{1'''}$ groups are bonded;
$R^2$ and $R^3$, when taken separately, represent, simultaneously or independently, a linear, branched or cyclic $C_1$ to $C_8$ alkyl or alkenyl group optionally substituted, a $C_6$ to $C_{10}$ aromatic group optionally substituted, or an $OR^{2'}$ or $NR^{2'}R^{3'}$ group, $R^{2'}$ and $R^{3'}$ being a $C_1$ to $C_8$ alkyl or alkenyl group; or the groups $R^2$ and $R^3$, when taken together, form a saturated or unsaturated ring optionally substituted, having 5 to 10 atoms and including the phosphorus atom to which the $R^2$ and $R^3$ groups are bonded;
$R^6$ and $R^7$ represent, simultaneously or independently, a hydrogen atom, a linear, branched or cyclic $C_1$ to $C_{10}$ alkyl or alkenyl group optionally substituted, a $C_6$-$C_{10}$ aromatic group optionally substituted, or an $OR^{4'}$ or $NR^{4'}R^{5'}$ group, $R^{4'}$ and $R^{5'}$ being a linear, branched or cyclic $C_1$ to $C_{10}$ alkyl or alkenyl group; $R^6$ and $R^1$ or $R^6$ and $R^{1'''}$, taken together, may form a saturated or unsaturated heterocycle, optionally substituted and optionally containing one or two additional nitrogen or oxygen atoms, containing 5 to 10 atoms and including the carbon atoms and the N atom to which the $R^6$ or $R^1$, or $R^{1''}$, group are bonded respectively; and Q represents:

a group of formula

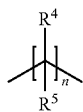

(i)

wherein n is an integer from 1 to 4, and $R^4$ and $R^5$ represent, simultaneously or independently, a hydrogen atom, a linear, branched or cyclic $C_1$ to $C_{10}$ alkyl or alkenyl group optionally substituted, a $C_6$-$C_{10}$ aromatic group optionally substituted, or an $OR^{4'}$ or $NR^{4'}R^{5'}$ group, $R^{4'}$ and $R^{5'}$ being a linear, branched or cyclic $C_1$ to $C_{10}$ alkyl or alkenyl group; two distinct $R^4$ and/or $R^5$ groups, taken together, may form a $C_5$ to $C_{10}$, saturated ring optionally substituted, including the carbon atoms to which each of the $R^4$ or $R^5$ group is bonded; or a group of formula

(ii)

wherein n is an integer from 2 to 4, and two distinct adjacent $R^4$ groups, taken together, form a $C_5$ to $C_{10}$, aromatic ring optionally substituted or a $C_5$-$C_{12}$ metallocenediyl optionally substituted, including the carbon atoms to which each of the $R^4$ group are bonded; or three distinct adjacent $R^4$ groups, taken together, form a naphthalene ring optionally substituted, including the carbon atoms to which each of the $R^4$ groups are bonded;

and wherein the substituents of $R^{1'}$, $R^{1'''}$ and $R^1$ to $R^7$ and Q are one or two halogen, $C_1$ to $C_{10}$ alkoxy or polyalkyleneglycols groups, halo- or perhalo-hydrocarbon, COOR, $NR^2$, quaternary amine or R groups, wherein R is a $C_1$ to $C_6$ alkyl, or a $C_5$ to $C_{12}$ cycloalkyl, aralkyl or aromatic group, the latter being also optionally substituted by one, two or three halogen, sulfonates groups or $C_1$-$C_8$ alkyl, alkoxy, amino, nitro, sulfonates, halo- or perhalo-hydrocarbon or ester groups.

5. The process according to claim 1, wherein L2 is a ligand of formula

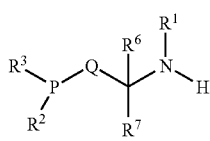

(2-B)

in which $R^1$ represents a hydrogen atom, a linear, branched or cyclic $C_1$ to $C_6$ alkyl or alkenyl group optionally substituted;

$R^2$ and $R^3$ represent, simultaneously or independently, a linear, branched or cyclic $C_1$ to $C_6$ alkyl group optionally substituted, a phenyl or naphthyl group optionally substituted; or the groups $R^2$ and $R^3$, taken together, form a saturated or unsaturated ring optionally substituted, having 5, 6 or 7 atoms and including the phosphorus atom to which the $R^2$ and $R^3$ groups are bonded;

$R^6$ and $R^7$ represent, simultaneously or independently, a hydrogen atom, a linear or branched $C_1$ to $C_4$ alkyl group optionally substituted, a phenyl ring optionally substituted; $R^6$ and $R^1$, taken together, may form a saturated or unsaturated heterocycle, optionally substituted and optionally containing one additional nitrogen or oxygen atoms, containing 5 or 6 atoms and including the carbon atoms and the N atom to which the $R^6$ or $R^1$ group are bonded respectively; and Q represents:

a group of formula

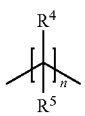

(iii)

wherein n is an integer from 2 or 3, and $R^4$ and $R^5$ represent, simultaneously or independently, a hydrogen atom, a linear or branched $C_1$ to $C_4$ alkyl group optionally substituted, a phenyl ring optionally substituted; or two distinct $R^4$ and/or $R^5$ groups, taken together, form a $C_5$ to $C_{10}$ saturated ring optionally substituted including the carbon atoms to which each of the $R^4$ or $R^5$ group is bonded; or a group of formula

(iv)

wherein n is an integer from 1 to 3, and two distinct adjacent $R^4$ groups, taken together, form a $C_5$ to $C_{10}$ aromatic ring optionally substituted or a $C_5$-$C_{12}$ ferrocenediyl optionally substituted, including the carbon atoms to which each of the $R^4$ group are bonded; or three distinct adjacent $R^4$ groups, taken together, form a naphthalene ring optionally substituted, including the carbon atoms to which each of the $R^4$ group are bonded.

6. The process according to claim 1, wherein L2 is a ligand of formula (2-C) or (2-D)

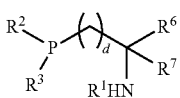

(2-C)

-continued

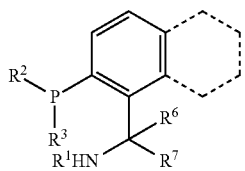

(2-D)

wherein the dotted lines in formula (2-D) indicate the presence of a phenyl or a naphthyl group;

d represents 1 or 2;

$R^1$ represents a hydrogen atom or a $C_1$ to $C_4$ linear or branched alkyl group possibly substituted;

$R^2$ and $R^3$ represent a linear, branched or cyclic $C_1$ to $C_6$ alkyl group optionally substituted or an phenyl group optionally substituted; and $R^6$ and $R^7$ represent, simultaneously or independently, a hydrogen atom, a linear or branched $C_1$ to $C_4$ alkyl group optionally substituted, or an phenyl group optionally substituted; or $R^6$ and $R^1$, taken together, form a saturated heterocycle, optionally substituted and optionally containing an additional nitrogen or oxygen atoms.

7. The process according to claim 1, wherein L2 is a ligand of formula

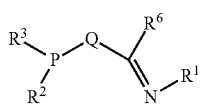

(2-E)

in which $R^1$ represents a hydrogen atom, a linear, branched or cyclic $C_1$ to $C_6$ alkyl or alkenyl group optionally substituted;

$R^2$ and $R^3$ represent, simultaneously or independently, a linear, branched or cyclic $C_1$ to $C_6$ alkyl group optionally substituted, a phenyl or naphthyl group optionally substituted; or the groups $R^2$ and $R^3$, taken together, form a saturated or unsaturated ring optionally substituted, having 5, 6 or 7 atoms and including the phosphorus atom to which the $R^2$ and $R^3$ groups are bonded;

Q represents:

a group of formula

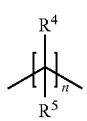

(iii)

wherein n is an integer from 2 or 3, and $R^4$ and $R^5$ represent, simultaneously or independently, a hydrogen atom, a linear or branched $C_1$ to $C_4$ alkyl group optionally substituted, a phenyl ring optionally substituted; or two distinct $R^4$ and/or $R^5$ groups, taken together, form a $C_5$ to $C_{10}$ saturated ring optionally substituted including the carbon atoms to which each of the $R^4$ or $R^5$ group is bonded; or a group of formula

(iv)

wherein n is an integer from 1 to 3, and two distinct adjacent $R^4$ groups, taken together, form a $C_5$ to $C_{10}$ aromatic ring optionally substituted or a $C_5$-$C_{12}$ ferrocenediyl optionally substituted, including the carbon atoms to which each of the $R^4$ group are bonded; or three distinct adjacent $R^4$ groups, taken together, form a naphthalene ring optionally substituted, including the carbon atoms to which each of the R4 group are bonded; and $R^6$ represents a hydrogen atom, a linear or branched $C_1$ to $C_4$ alkyl group or an phenyl group optionally substituted; or $R^6$, when taken together with $R^1$, forms a $C_3$-$C_9$ C=N function-containing heterocycle optionally substituted and optionally containing one additional nitrogen or oxygen atom.

8. The process according to claim 1, wherein L2 is a ligand of formula (2-F) or (2-G)

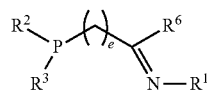

(2-F)

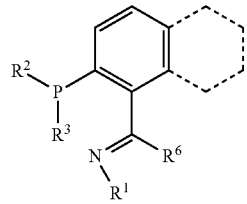

(2-G)

wherein the dotted lines in formula (2-G) indicate the presence of a phenyl or a naphthyl group;

e represents 1 or 2;

$R^1$ and $R^{1'}$ represent, simultaneously or independently, a hydrogen atom, a linear, branched or cyclic $C_1$ to $C_6$ alkyl or alkenyl group optionally substituted;

$R^2$ and $R^3$, represent, simultaneously or independently, a linear, branched or cyclic $C_1$ to $C_6$ alkyl group optionally substituted, a phenyl or naphthyl group optionally substituted; or the groups $R^2$ and $R^3$, taken together, form a saturated or unsaturated ring optionally substituted, having 5, 6 or 7 atoms and including the phosphorus atom to which the $R^2$ and $R^3$ groups are bonded;

$R^6$ represents a hydrogen atom, a linear or branched $C_1$ to $C_4$ alkyl group optionally substituted, or a phenyl group optionally substituted; or $R^6$, when taken together with $R^1$, forms a $C_3$-$C_9$ C=N function-containing heterocycle optionally substituted and optionally containing one additional nitrogen or oxygen atom.

9. A process for the reduction by hydrogenation, using molecular $H_2$, of a $C_3$-$C_{70}$ substrate containing one or two ester or lactone functional groups into its corresponding alcohol or diol, which comprises carrying out the process under suitable pressure and temperature conditions in the presence of a base having a $pK_a$ above 14 and at least one complex in the form of a ruthenium complex of formula $$[Ru(L2)_b(L')_a Y_2] \qquad (1)$$

wherein L2 represents a $C_4$-$C_{40}$ bidentate ligand wherein the coordinating groups consist of one amino or imino group and one phosphino group;

L' represents a $C_3$-$C_{70}$ mono-phosphine or a solvent;

b is 1 and a is 1 or 2 or b is 2 and a is 0; and each Y represents, simultaneously or independently, CO, a hydrogen or halogen atom, a hydroxyl group, a $BH_4$ or $AlH_4$ group or a $C_1$-$C_6$ alkoxy or carboxylic radical.

10. The process according to claim 1, wherein the base is an alkaline or alkaline-earth metal carbonates, an alkaline or alkaline-earth metal hydroxides, $C_{1-10}$ amidures, $C_{10-26}$ phosphazine or an alcoholate of formula $(R^{13}O)_2M$ or $R^{13}OM'$, wherein M is an alkaline-earth metal, M' is an alkaline metal or an ammonium $NR^{14}_4{}^+$, $R^{13}$ stands for hydrogen or a $C_1$ to $C_6$ linear or branched alkyl radical and $R^{14}$ stands for a $C_1$ to $C_{10}$ linear or branched alkyl radical.

11. The process according claim 1, wherein the substrate is a compound of formula (I)

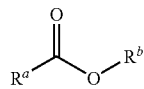
(I)

wherein $R^a$ and $R^b$ represent, simultaneously or independently, a linear, branched or cyclic $C_1$-$C_{30}$ aromatic, alkyl or alkenyl group optionally substituted; or $R^a$ and $R^b$ are bonded together and form a $C_4$-$C_{20}$ saturated or unsaturated group, optionally substituted;

and wherein the substituents of $R^a$ and $R^b$ are a $COOR^c$, group, one, two or three halogen, $OR^c$, $NR^c{}_2$ or $R^c$ groups, in which $R^c$ is a hydrogen atom, a halogenated $C_1$-$C_2$ group or a $C_1$ to $C_{10}$ cyclic, linear or branched alkyl, or alkenyl group.

12. The process according claim 1, wherein the pressure is in a range of between 1 and 80 bars and the temperature is in a range of between 0° C. and 120° C. with higher pressures of the pressure range used with lower temperatures of the temperature range and lower pressures used with higher temperatures.

13. A process for the reduction by hydrogenation, using molecular $H_2$, of a $C_3$-$C_{70}$ substrate containing one or two ester or lactone functional groups into its corresponding alcohol or diol, which comprises carrying out the process under suitable pressure and temperature conditions in the presence of a base and at least one complex in the form of a ruthenium complex of formula $$[Ru(L2)_b(L')_a Y_2] \qquad (1)$$

in which L2 represents a $C_4$-$C_{40}$ bidentate ligand wherein the coordinating groups consist of one amino or imino group and one phosphino group;

L' represents a $C_3$-$C_{70}$ mono-phosphine or a solvent;

b is 1 and a is 1 or 2 or b is 2 and a is 0; and each Y represents, simultaneously or independently, CO, a hydrogen or halogen atom, a hydroxyl group, a $BH_4$ or $AlH_4$ group or a $C_1$-$C_6$ alkoxy or carboxylic radical;

wherein the pressure is in a range of between 1 and 80 bars and the temperature is in a range of between 0° C. and 120° C. with higher pressures of the pressure range used with lower temperatures of the temperature range and lower pressures used with higher temperatures; and the suitable pressure and temperature conditions include a minimum temperature and pressure within said ranges to achieve a substrate conversion that is greater than 50, 75, 90 or 95% and a yield of the corresponding alcohol or diol that is greater than 40, 50, 80 or 90%.

14. The process according to claim 1, wherein the complex is $[RuCl_2(L-1)_2]$ and L-1 is

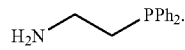

15. The process according to claim 9, wherein the complex is $[RuCl_2(L-1)_2]$ and L-1 is

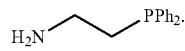

16. The process according to claim 13, wherein the complex is $[RuCl_2(L-1)_2]$ and L-1 is

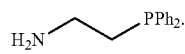

* * * * *

UNITED STATES PATENT AND TRADEMARK OFFICE
CERTIFICATE OF CORRECTION

PATENT NO. : 8,692,022 B2
APPLICATION NO. : 12/839787
DATED : April 8, 2014
INVENTOR(S) : Saudan et al.

It is certified that error appears in the above-identified patent and that said Letters Patent is hereby corrected as shown below:

In the Claims

Column 28:

Lines 31-37, delete formula "(2-A')" and insert: -- 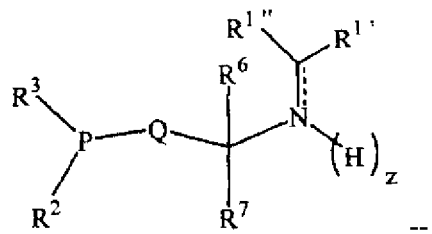 --

Column 31:

Lines 2-9, delete formula "(2D)" and insert: -- 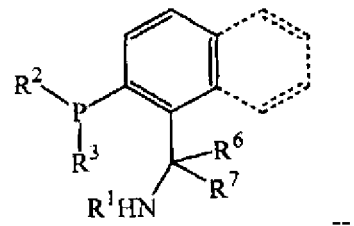 --

Column 32:

Lines 37-45, delete formula "(2-G)" and insert: -- 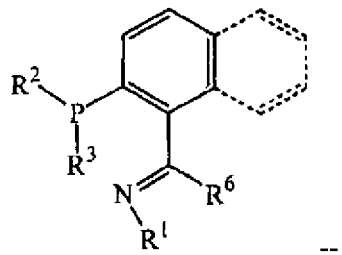 --

Signed and Sealed this
Tenth Day of June, 2014

Michelle K. Lee
*Deputy Director of the United States Patent and Trademark Office*